United States Patent [19]

Ikeda et al.

[11] 4,229,227

[45] Oct. 21, 1980

[54] GEL COMPOSITION FOR NAIL ENAMEL

[75] Inventors: Toshihide Ikeda, Yokohama; Motokiyo Nakano, Sagamihara, both of Japan

[73] Assignee: Shiseido Co., Ltd., Tokyo, Japan

[21] Appl. No.: 970,243

[22] Filed: Dec. 18, 1978

[51] Int. Cl.$^2$ .......................... A61K 7/043; C08L 1/18
[52] U.S. Cl. ..................................... 106/181; 424/61; 106/195
[58] Field of Search ................... 424/61; 106/188, 191, 106/195, 181

[56] References Cited

U.S. PATENT DOCUMENTS

| | | | |
|---|---|---|---|
| 1,878,477 | 9/1932 | Ellis et al. | 424/61 |
| 3,257,279 | 6/1966 | Schain | 106/195 |
| 3,407,160 | 10/1968 | Frank | 106/271 |
| 3,422,185 | 1/1969 | Kuritzkes | 424/61 |
| 3,864,294 | 2/1975 | Busch, Jr. | 424/61 |

*Primary Examiner*—Theodore Morris
*Attorney, Agent, or Firm*—Miller & Prestia

[57] ABSTRACT

Gel composition suitable for use in the preparation of nail enamel is provided. The gel composition contains a chip composition which is prepared by mixing, under heating and compression, organically modified montmorillonite clay, nitrocellulose, and a substance which is capable of swelling the montmorillonite clay and is capable of plasticizing the nitrocellulose. The thixotropic nail enamel prepared from this gel composition has the advantages that a pretty glossy film can be obtained and the gelling state thereof is stable.

10 Claims, No Drawings

GEL COMPOSITION FOR NAIL ENAMEL

The present invention relates to a gel composition suitable for use in a nail enamel.

Nail enamels (or nail lacquers) are film-forming compositions which generally are air-dried at an ambient temperature. Nail enamels containing organically modified montmorillonite clays, which are known as a nonaqueous gelling agent, are well-known in the art.

In order to prevent the separation (or settling) of pigments and pearl essences from nail enamels containing the same, the use of organically modified montmorillonite clays is proposed. For example, U.S. Pat. No. 3,422,185 discloses the use of the organically modified montmorillonite clays for preventing precipitation of pigments and pearl essences in nail enamels, color separation and separation of the constituents of the nail enamels. Japanese Patent Publication (KOKOKU) No. 47-40375/72 discloses that an organically modified montmorillonite clay as well as an inorganic or organic acid are mixed with and dispersed in a cosmetic base for dispersing pearl essences therein. Further, Japanese Laid-Open Application (KOKAI) No. 49-97830/74 discloses gel coating compositions containing an amine type modified montmorillonite clay, a swelling agent, such as orthophosphoric acid, and substances such as acetone, isopropyl alcohol and butyl acetate, which have a polar group and an affinity for other constituents. However, in these conventional nail enamels, since the organically modified montmorillonite clay is simply mixed into the nail enamel base, the nail enamel so obtained has a poor pigment dispersion stability and a poor gloss. This is because the swelling and the dispersion force of the organically modified montmorillonite clay in the nail enamel are poor.

The organically modified montmorillonite clays can be prepared by chemically and interlaminatingly bonding cationic active agents and polar higher organic compounds to the clay mineral (i.e. the montmorillonite clay). The interlaminar distance of the organically modified montmorillonite clay molecule is expanded by the action of a solvent, such as toluene and the like, and swells in the solvent. When the organically modified montmorillonite clays are in the form of powders, agglomerates of the montmorillonite powders are formed. In order to exhibit their inherent effectiveness in the nail enamel, the organically modified montmorillonite clays must be finely and uniformly dispersed in the nail enamel. However, since a simple mechanical dispersion of the organically modified montmorillonite clays into the nail enamel by using, for example, a disper, is not sufficient for complete dispersion of the clay, the gloss and the transparency of the resulting nail enamel film decrease due to the presence of the powder agglomerates of the organically modified montmorillonite clay in the film.

Accordingly, the objects of the present invention are to obviate the afore-mentioned problems of the gel composition for conventional nail enamels and to provide a novel gel composition suitable for use in a thixotropic nail enamel.

In accordance with the present invention, there is provided a gel composition for a nail enamel comprising:

(i) 10 through 30% by weight of a chip composition which is prepared by mixing, under heating and compression, a mixture of (A) 25 through 70% by weight of organically modified montmorillonite clay, (B) 5 through 70% by weight of nitrocellulose and (C) 5 through 30% by weight of a substance which is capable of swelling the component (A) and also capable of plasticizing the component (B), and;

(ii) 70 through 90% by weight of an organic mixed solvent.

As mentioned hereinbefore, when the organically modified montmorillonite clays are mechanically dispersed into the nail enamel by using, for example, a disper, the properties, especially the gelling property, of the modified montmorillonite clay can not be improved. However, it has been found that, when organically modified montmorillonite clay is compounded into a chip composition by milling the clay powder with the other ingredients on, for example, a roll mill, under heating and compression, the organically modified montmorillonite agglomerated powders can be deagglomerated and, therefore, can be finely and uniformly dispersed into a nail enamel. As a result, the nail enamel prepared from the present gel composition, containing the organically modified montmorillonite clay thus subjected to the milling treatment, provides a pretty glossy film when it is applied. Thus, loss of the luster of the film and decrease in the transparency of the film due to the presence of the agglomerated powder of the organically modified montmorillonite clay is not observed at all. In view of the previous understanding in the art that clay minerals can afford a good gelling property to nail enamels but function as a certain kind of matte agent, the above-mentioned phenomenon constitutes significant progress in the art. That is to say, it has been found that the good gelling property of the organically modified montmorillonite clays cannot be exhibited in the nail enamel unless the clays are sufficiently swollen by the penetration of solvents contained in the nail enamel into the interlaminar portions of the microstructure of the clays. Even when the organically modified montmorillonite clays are compounded into a chip composition for nail enamels without mixing (or milling), under heating and compression, the interlaminar distance of the micro structure of the organically modified montmorillonite clays cannot be expanded. Therefore, when such chip composition is added to a nail enamel, the thixotropic property of the clay is not improved in the nail enamel. As a result, although the luster of the film on the fingernail is good, a stable nail enamel cannot be obtained, due to the fact that pigment particles contained in the nail enamel tend to separate and to settle on the bottom of the nail enamel container.

In Japanese Patent Laid-Open Application (KOKAI) No. 52-145528/77 we proposed a process for preparing a gell composition comprising the steps of mixing, under heating and compression, organically modified montmorillonite clays, nitrocellulose, conventional plasticizer (e.g. dibutyl phthalate, acetyl tributyl citrate), and organic solvents which are capable of satisfactorily swelling the organically modified montmorillonite clays, to thereby prepare a chip composition, and; then, incorporating the chip composition into an organic mixed solvent. When the gel composition thus prepared is incorporated into the nail enamel, the nail enamel having a good pigment dispersion stability and a good gelling property, and also, providing a good glossy film, can be obtained. However, since a large amount of organic solvents are vaporized or splashed into the surrounding environment during the milling operation, our above-mentioned prior process is not preferable from economic, environmental health and safety points of view.

Contrary to the above, according to the present invention, since non-volatile substances having a high boiling point are used as substances which are capable of swelling the organically modified montmorillonite clay, the afore-mentioned problems are completely solved.

Examples of such substances are:

(i) compounds having a general formula, $HO(RO)_mH$ (wherein R is $C_2H_4$ and $C_3H_6$, and m is an integer of 3 through 90) such as, for example, polyethylene glycol, preferably, having a weight-average molecular weight of about 200 through about 4000, and preferably, 300 through 3500, polypropylene glycol, preferably, having a weight-average molecular weight of about 300 through about 5000, and the like;

(ii) compounds having a general formula, $R'O(RO)_nH$ (wherein R is $C_2H_4$ and $C_3H_6$, R' is an alkyl group having 4 through 20 carbon atoms and n is an integer of 1 through 50) such as, for example, polyoxyethylene lauryl ether having an ethylene oxide addition molar number of about 8 through about 15, and preferably, 8 through 14, polyoxyethylene stearyl ether having an ethylene oxide addition molar number of about 9 through about 15 and the like;

(iii) esters of dicarboxylic acids having 4 through 10 carbon atoms with aliphatic lower alcohols having 1 through 4 carbon atoms, such as, for example, diethyl adipate, dibutyl sebacate and the like. These compounds can be used alone or in any mixture thereof. These compounds can not only swell the organically modified montmorillonite clays in the chip compositions, but also plasticize the nitrocellulose. Accordingly, an excellent chip composition suitable for use in the preparation of nail enamels can be obtained only by milling a mixture of (A) 25 through 70% by weight of an organically modified montmorillonite clay, (B) 5 through 70% by weight of nitrocellulose and (C) 5 through 30% by weight of a substance which is capable of swelling the component (A) and is also capable of plasticizing the component (B) under heating and compression conditions.

If the amount of the component (A) is less than 25% by weight, a chip composition having a sufficient gelling property cannot be obtained, whereas if the amount of the component (A) is more than 70% by weight, a composition in the form of a chip cannot be obtained. On the other hand, if the amount of the component (B) is less than 5% by weight, a composition in the form of a chip cannot be obtained, whereas if the amount of the component (B) is more than 70% by weight, a chip composition having a sufficient gelling property cannot be obtained. Further, if the amount of the component (C) is less then 5% by weight, or more than 30% by weight, a composition in the form of a chip cannot be obtained.

The organically modified montmorillonite clays compounded into the chip composition of the present invention can include any known organically modified montmorillonite clays, such as, for example, dimethylbenzyldodecyl ammonium montmorillonite (which is commercially available from National Lead Industries, Inc. as "BENTONE 27"), dimethyldioctadecyl ammonium montmorillonite (which is commercially available from National Lead Industries, Inc. as "BENTONE 38") and the like.

The nitrocellulose compounded into the chip composition of the present invention can include any nitrocellulose which is generally used as a film-forming constituent in conventional nail enamels. Typically, so-called nitrocellulose "¼ second", nitrocellulose "½ second" and the like are used.

In the chip composition disclosed in the above-mentioned Japanese Patent Laid-Open Application (KOKAI) No. 52-145528, substantial amounts of the solvents to be used are vaporized or splashed during the milling operation on milling rolls. Contrary to this, the component (C) of the chip composition of the present invention is present in the chip composition after the milling operation in such a state that the component (C) penetrates into the interlaminar portions of the organically modified montmorillonite clay molecules and swells the clay molecules. Thus, in the subsequent step (i.e. the step in which the chip composition so obtained is dissolved and dispersed in a mixed organic solvent), the mixed solvent can be easily put into the interlaminar portion of the swelled montmorillonite clay, and a good gel composition for nail enamel having a sufficient amount of the mixed solvent in the interlaminar portions of the organically modified montmorillonite clay molecules can be obtained. For this reason, since the organically modified montmorillonite clay is still present in the clear swelling condition in the gel composition of the present invention, a good gelling property is exhibited in the gel composition, and also there is neither separation nor settling of the pigments and the pearl essences in the nail enamel. In addition, since the organically modified montmorillonite clay is finely divided by the milling operation, the film or coating on the fingernail is very lustrous.

The swelling force and the plasticizing force of typical compounds which can swell the organically modified montmorillonite clay and also can plasticize nitrocellulose are shown in Table 3 below.

(a) Determination of Swelling Force

In order to determine the swelling force of the substances listed in Table 3, the substances are separately mixed with "BENTONE 27" (i.e. dimethylbenzyldodecyl ammonium montmorillonite clay) and nitrocellulose "¼ second", in accordance with the compounding ratio (I) shown in Table 1, and then, the mixtures are subjected to a milling treatment on milling rolls to prepare chip compositions. The interlaminar distance (00 1 face) of the organically modified montmorillonite clay contained in the chip composition is measured by means of an X-ray diffraction device (RIGAKU Rota Slex Type RU-3). It was determined by the inventors of the present invention that the interlaminar distance of BENTONE 27 powder is 9.4A and that D.B.P. (i.e. dibutyl phthalate) cannot expand the interlaminar distance of the organically modified montmorillonite clay. In the case of a substance which has sufficient swelling force but has little plasticizing force, the compounding ratio (II) is used. The results are shown in Table 3 below.

TABLE 1

| | (% by weight) | | |
|---|---|---|---|
| I | | II | |
| BENTONE 27 | 47 | BENTONE 27 | 47 |
| Nitrocellulose "¼ second" | 41 | Nitrocellulose "¼ sicond" | 31 |
| Substance listed in Table 3 | 12 | D.B.P. | 10 |
| | | Substance listed in | 12 |

TABLE 1-continued

| | (% by weight) | |
|---|---|---|
| | I | II |
| | Table 3 | |

(b) Determination of Plasticizing Force

In order to determine the plasticizing force of the substances listed in Table 3, chip compositions are prepared in the same manner as described in the above paragraph (a). Each chip composition is then coated onto a glass plate at a film thickness of 0.175 mm by an applicator. After 1 hour, the hardness of the coating is measured by using a Vickers hardness testor (Micro Hardness Testor Type MVK, AKASHI SEISAKU-SHO, JAPAN), under the test conditions of a load of 100 gr, a thickness of the coating of 0.175 mm and a load hold time of 5 seconds, in accordance with the procedure of JIS (Japanese Industrial Standard)-B-7774. The results are shown in Table 3 below. The value of the hardness increases as the hardness of the coating decreases.

TABLE 2

| (% by weight) | |
|---|---|
| Nitrocellulose "¼ second" | 15 |
| Modified alkyd resin | 15 |
| Organic mixed solvent* | 65 |
| Substance listed in Table 3 | 5 |

*a mixture of 48% of butyl acetate, 38% of toluene, 10% of ethyl acetate and 4% of n-butyl alcohol.

TABLE 3

| No. | Substance (Sample) | Formulation | Interlaminer Distance (Å) | Hardness of Coating |
|---|---|---|---|---|
| 1 | Polyethylene Glycol (M.W. 200) | I | 22 | 189 |
| 2 | Polyethylene Glycol (M.W. 300) | " | 25 | 185 |
| 3 | Polyethylene Glycol (M.W. 400) | " | 25 | 183 |
| 4 | Polyethylene Glycol (M.W. 600) | " | 21 | 172 |
| 5 | Polyethylene Glycol (M.W. 1000) | " | 20 | 171 |
| 6 | Polyethylene Glycol (M.W. 1500) | " | 18 | 167 |
| 7 | Polyethylene Glycol (M.W. 4000) | " | 15 | 153 |
| 8 | Polyoxyethylene Lauryl Ether (E.O. Add. Mol. No. 8) | " | 18 | 128 |
| 9 | Polyoxyethylene Lauryl Ether (E.O. Add. Mol. No. 9) | " | 17 | 135 |
| 10 | Polyoxyethylene Lauryl Ether (E.O. Add. Mol. No. 15) | " | 14 | 147 |
| 11 | Polyoxyethylene Stearyl Ether (E.O. Add. Mol. No. 9) | " | 20 | 216 |
| 12 | Polyoxyethylene Stearyl Ether (E.O. Add. Mol. No. 15) | " | 16 | 143 |
| 13 | Diethyl Adipate | " | 22 | 155 |
| 14 | Dibutyl Sebacate | " | 19 | 174 |
| 15 | Ethylene Glycol Monobutyl Ether | II | 26 | 85 |
| 16 | Benzyl Alcohol | " | 28 | 81 |
| 17 | Liquid Paraffin | " | 12 | 83 |
| 18 | Polyoxyethylene Oleyl Ether (E.O. Add. Mol. No. 2) | " | 14 | 94 |
| 19 | Butyl Carbitol Acetate | I | 13 | 164 |
| 20 | Diisopropyl Adipate | " | 13 | 129 |
| 21 | Diisobutyl Adipate | " | 13 | 129 |
| 22 | D.B.P. (Dibutyl Phthalate) | " | 10 | 118 |
| 23 | Acetyltributyl Citrate | " | 10 | 118 |

Nos. 15-23: Comparative Examples

The substances which can be used as the component (C) in the present invention must have an interlaminar distance of not less than about 16 Å and a Vickers hardness of not less than 110. However, substances such as ethylene glycol monobutyl ether and benzyl alcohol, which have an interlaminar distance of not less than 16 Å, cannot be used as the component (C) in the present chip composition because of their high hardness (i.e. Vickers hardness of less than 110), provided that known plasticizers (e.g. D.B.P.) are compounded into the composition in combination with such substances. On the other hand, substances such as butyl carbitol acetate and diisobutyl adipate, which have an interlaminar distance of less than 16 Å, cannot be used as the component (C) in the present chip composition.

The milling operation of the components (A), (B) and (C) can be carried out by any known techniques. Such techniques are generally used in, for example, the paint and varnish industry, the rubber industry and the like, by using a milling roll, a Bunbury mixer, a colloid mill and the like under compression, at a temperature of about 40° through 70° C.

The gel composition for nail enamels according to the present invention can be prepared by simply and mechanically mixing 10 through 30% by weight of the above-mentioned chip composition with 70 through 90% by weight of an organic mixed solvent. If the amount of the chip composition is less than 10% by weight, or more than 30% by weight, a gel composition which can provide a nail enamel having a suitable viscosity cannot be obtained. On the other hand, if the amount of the organic mixed solvent is less than 70% by weight, or more than 90% by weight, a gel composition which can provide a nail enamel having a suitable viscosity cannot be obtained.

The organic mixed solvents used in the gel composition of the present invention generally include those which can be incorporated into the conventional nail enamel compositions. Examples of such mixed solvents are any mixtures of (a) 30-70% by weight of at least one selected from toluene, xylene and the like; (b) 30-70% by weight of at least one selected from butyl acetate, ethyl acetate, methyl ethyl ketone, methyl isobutyl ketone, tetrahydrofuran and ethylene glycol monoethyl ether and the like and (c) 5-20% by weight of at least one selected from ethyl alcohol, acetone and isopropyl alcohol and the like.

The present gel composition can be mixed with the conventional other constituents for nail enamels to prepare a thixotropic nail enamel. Such constituents generally include nitrocellulose; resin such as alkyd resin and acrylic resin; plasticizer such as D.B.P. and acetyl tributyl citrate; solvent such as butyl acetate, ethyl acetate, ethyl alcohol, isopropyl alcohol, butyl alcohol, toluene, xylene and the like; pigments such as titanium oxide, iron oxides and the like; pearl essences; dyes; UV absorbers; and the like. Although there is no particular limit in the compounding amount of the gel composition of the present invention into the nail enamels, about 5% by weight through about 20% by weight of the gel composition, based on the total weight of the nail enamel, can be effectively incorporated into the nail enamels. The thixotropic nail enamel prepared from the present gel composition has the advantages that the gelling state thereof is stable and that a pretty good film can be obtained when it is applied to the finger nails.

The present invention will be further illustrated by, but is by no means limited to, the Examples set forth below. Percentages appearing in the examples are by weight unless otherwise noted.

EXAMPLE 1

A chip composition was prepared by mixing the following ingredients and, then, milling the mixture on two-stage rollers, under heating and compression. The surface temperatures of the rollers were 40° C. (first roll) and 60° C. (second roll).

| Chip Composition | % |
| --- | --- |
| BENTONE 27 (Dimethylbenzyldodecyl Ammonium Montmorillonite) | 47 |
| Nitrocellulose "¼ second" | 41 |
| Polyethylene Glycol (M.W. 300) | 12 |
| Total | (100) |

18% of the thus prepared composition was then mixed with 82% of a mixed solvent having the following composition.

| Mixed Solvent Composition | % |
| --- | --- |
| Isopropyl Alcohol | 19 |
| Toluene | 39 |
| n-Butyl Acetate | 42 |
| Total | (100) |

The chip composition was dissolved and dispersed in the mixed solvent to prepare a gel composition.

EXAMPLE 2

A gel composition was prepared from 18% of a chip composition having the following composition and 82% of mixed solvent having the following composition by following the same procedure as mentioned in Example 1.

| Chip Composition | % |
| --- | --- |
| BENTONE 27 | 48 |
| Nitrocellulose "¼ second" | 42 |
| Polyethylene Glycol (E.O. Addition Molar Number: 9) | 10 |
| Total | (100) |

| Mixed Solvent Composition | % |
| --- | --- |
| Isopropyl Alcohol | 18 |
| Toluene | 38 |
| n-Butyl Acetate | 44 |
| Total | (100) |

EXAMPLE 3

A gel composition was prepared from 18% of a chip composition having the following composition and 82% of a mixed solvent having the following composition by following the same procedure as mentioned in Example 1.

| Chip Composition | % |
| --- | --- |
| BENTONE 38 (Dimethyloctadecyl Ammonium Montmorillonite) | 47 |
| Nitrocellulose "¼ second" | 40 |
| Diethyl Adipate | 13 |
| Total | (100) |

| Mixed Solvent Composition | % |
| --- | --- |
| Isopropyl Alcohol | 17 |
| Toluene | 45 |
| n-Butyl Acetate | 38 |
| Total | (100) |

COMPARATIVE EXAMPLE 1

In a mixed solvent of 15.6% of isopropyl alcohol, 32.0% of toluene and 34.4% of n-butyl acetate, 7.3% of nitrocellulose "¼ second" was dissolved, and then 2.2% of polyethylene glycol (M.W. 300) and 8.5% of BENTONE 27 (i.e. dimethylbenzyldodecyl ammonium montmorillonite) were added to the solution. Thus, a uniform gel composition was prepared after mixing.

COMPARATIVE EXAMPLE 2

Following the same procedure as mentioned in Example 1, gel composition was prepared from 18% of a chip composition having the following composition and 82% of a mixed solvent having the following composition.

| Chip Composition | % |
| --- | --- |
| BENTONE 27 | 44 |
| Nitrocellulose "¼ second" | 40 |
| D.B.P. (Dibutyl Phthalate) | 16 |
| Total | (100) |

| Mixed Solvent Composition | % |
| --- | --- |
| Isopropyl Alcohol | 19 |
| Toluene | 39 |
| n-Butyl Acetate | 42 |
| Total | (100) |

Thus, the gel composition in which polyethylene glycol in the gel composition of Example 1 was replaced with a conventional plasticizer, D.B.P. was prepared.

The gel composition prepared in Examples 1 through 3 and Comparative Examples 1 and 2 were evaluated with respect to glossiness and transmission. The results are shown in Table 4 below.

TABLE 4

|                       | Glossiness (%)[1] | Transmission (%)[2] |
|-----------------------|-------------------|----------------------|
| Example 1             | 73.8              | 87.0                 |
| Example 2             | 72.2              | 85.4                 |
| Example 3             | 69.1              | 76.6                 |
| Comparative Example 1 | 2.4               | 30.9                 |
| Comparative Example 2 | 73.9              | 86.6                 |

[1] After each gel composition was applied by an applicator onto a clear polyvinyl chloride sheet to prepare a uniform film thereon, surface glossiness of the uniform film was determined by using specular surface technique (angle of incidence 60°, angle of reflection 60°). The value of the glossiness is based on that of the clear polyvinyl chloride sheet, which is considered to have a glossiness of 100%.

[2] After each gel composition was applied by an applicator onto a clear polyvinyl chloride sheet to prepare a uniform film having a thickness of 0.425 mm, the transmission of each sample was determined by using a Hitachi Spectrophotometer Type 124 (Hitachi SEISAKUSHO, TOKYO). The wavelength of the light which was used for the determination was 520 mμ. The value of the transmission is based on that of the clear polyvinyl chloride sheet, which is considered to have a transmission of 100%.

As will be clear from Table 4, both the glossinesses and transmissions of the gel compositions prepared in Examples 1 through 3 according to the present invention are superior to those of Comparative Example 1. Since the sample of Comparative Example 2 was subjected to the roll treatment, the glossiness and transmission thereof were also good.

EXAMPLES 4 THROUGH 6 AND

Comparative Examples 3 and 4

Using the gel compositions prepared in Examples 1 through 3 and also in Comparative Examples 1 and 2, nail enamel compositions were prepared in a conventional manner in accordance with the compounding ratio shown in Table 5 below. The nail enamel compositions were evaluated with respect to stability (separation and settling) of the nail enamel and the gloss of the coating or film when they were applied onto a fingernail. The results are shown in Table 6 below.

TABLE 5

(% by weight)

|                                                    | Example |       |       | Comparative Example |       |
|----------------------------------------------------|---------|-------|-------|---------------------|-------|
| Composition                                        | 4       | 5     | 6     | 3                   | 4     |
| Nitrocellulose                                     | 11.5    | 11.5  | 11.5  | 11.5                | 11.5  |
| Modified alkyd resin                               | 12      | 12    | 12    | 12                  | 12    |
| Polyethylene glycol (M.W. 1500)                    | 2.2     | —     | —     | 2.2                 | 2.2   |
| Polyoxyethylene lauryl ether (E.O. Addition Mol. No. 15) | —       | 4.5   | —     | —                   | —     |
| Acetyl tributyl citrate                            | —       | —     | 5.5   | —                   | —     |
| Toluene                                            | 21.72   | 20.82 | 20.42 | 21.72               | 21.72 |
| Ethyl acetate                                      | 10.7    | 10.4  | 10.3  | 10.7                | 10.7  |
| n-Butyl Acetate                                    | 22.2    | 21.1  | 20.6  | 22.2                | 22.2  |
| Iron oxide pigment                                 | 0.47    | 0.47  | 0.47  | 0.47                | 0.47  |
| Titanium dioxide                                   | 0.13    | 0.13  | 0.13  | 0.13                | 0.13  |
| D & C Red No. 34                                   | 0.02    | 0.02  | 0.02  | 0.02                | 0.02  |
| D & C Orange No. 17                                | 0.06    | 0.06  | 0.06  | 0.06                | 0.06  |
| Pearl essence                                      | 4.0     | 4.0   | 4.0   | 4.0                 | 4.0   |
| Gel Composition                                    |         |       |       |                     |       |
| Example 1                                          | 15      | —     | —     | —                   | —     |
| Example 2                                          | —       | 15    | —     | —                   | —     |
| Example 3                                          | —       | —     | 15    | —                   | —     |
| Comparative Example 1                              |         |       |       | 15                  |       |
| Comparative Example 2                              | —       | —     | —     | —                   | 15    |
| Total                                              | 100     | 100   | 100   | 100                 | 100   |

TABLE 6

|               | Example |      |      | Comparative Example |      |
|---------------|---------|------|------|---------------------|------|
|               | 4       | 5    | 6    | 3                   | 4    |
| Stability*    | Good    | Good | Good | Poor                | Poor |
| Gloss in film | Good    | Good | Good | Poor                | Good |

*The stability of the nail enamels with the lapse of time was evaluated by observing the separation and settling of the pigments and pearl essence in the nail enamels after allowing to stand at 40° C. for 1 month.
Good Neither separation nor settling was observed.
Poor Both separation and settling were observed.

With respect to the gloss of the coatings or films, good results were obtained, except for the nail enamel of Comparative Example 3, containing the gel composition of Comparative Example 1 which was not subjected to the milling treatment.

It is known that, when the compounding ratio of the polar solvent in the nail enamel increases, the thixotropic property of the nail enamel is advantageously improved. Thus, the nail enamel including the present gel composition has the further advantages that coating property thereof is good and the nail enamel can be easily and smoothly coated onto the surface of a fingernail by a coating brush.

Although it is hereinbefore described that the present gel composition is mainly used for a nail enamel, it should be noted that this gel composition can be also used for a coating composition in order to provide a coating composition having a good gelling state and good application properties without causing a decrease in gloss.

What we claim is:

1. A gel composition for a nail enamel comprising (i) 10 through 30% by weight of a chip composition which is prepared by mixing, under heat and compression, a mixture of (A) 25 through 70% by weight of an organically modified montmorillonite clay, (B) 5 through 70% by weight of nitrocellulose and (C) 5 through 30% by weight of at least one substance selected from the group consisting of compounds having a general formula, HO(RO)$_m$H (wherein R is C$_2$H$_4$ and C$_3$H$_6$) and m is an integer of 3 through 90); compounds having a general formula R'O(RO)$_n$H (wherein R is C$_2$H$_4$ and C$_3$H$_6$ R' is an alkyl group having 4 through 20 carbon atoms and n is an integer of 1 through 50) and esters of dicarboxylic acids having 4 through 10 carbon atoms with aliphatic lower alcohols having 1 through 4 carbon atoms, and; (ii) 70 through 90% by weight of an organic mixed solvent.

2. A gel composition as claimed in claim 1, wherein said organically modified montmorillonite clay (A) is dimethylbenzylodecyl ammonium montmorillonite, dimethyldioctadecyl ammonium montmorillonite or a mixture thereof.

3. A gel composition as claimed in claim 1, wherein said nitrocellulose (B) is nitrocellulose "¼ second", nitrocellulose "½ second" or a mixture thereof.

4. A gel composition as claimed in claim 1, wherein said substance (C) is polyethylene glycol having a weight-average molecular weight of about 300 through about 4000.

5. A gel composition as claimed in claim 1, wherein said substance (C) is polyoxyethylene lauryl ether having an ethylene oxide addition molar number of about 8 through about 15.

6. A gel composition as claimed in claim 1, wherein said substance (C) is polyoxyethylene stearyl ether having an ethylene oxide addition molar number of about 9 through about 15.

7. A gel composition as claimed in claim 1, wherein said organic mixed solvent is a mixture of (a) at least one selected from toluene, xylene and isoparafin; (b) at least one selected from butyl acetate ethyl acetate, methyl ethyl ketone, methyl isobutyl ketone, tetrahydrofuran and ethylene glycol monoethyl ether and (c) at least one selected from ethyl alcohol, acetone and isopropyl alcohol.

8. A gel composition as claimed in claim 1, wherein said chip composition comprises dimethylbenzyldodecyl ammonium montmorillonite, nitrocellulose "¼ second" and polyethylene glycol having a molecular weight of about 300.

9. A gel composition as claimed in claim 1, wherein said chip composition comprises dimethylbenzyldodecyl ammonium montmorillonite, nitrocellulose "¼ second" and polyoxyethylene stearyl ether having an ethylene oxide addition molar number of 9.

10. A gel composition as claimed in claim 1, wherein said chip composition comprises dimethyldioctadecyl ammonium montmorillonite, nitrocellulose "¼ second" and diethyl adipate.

* * * * *